United States Patent [19]

Mattsson et al.

[11] Patent Number: 5,085,868
[45] Date of Patent: Feb. 4, 1992

[54] LIQUID DOSAGE FORM FOR ALL ORAL ADMINISTRATION OF A PHARMACEUTICALLY ACTIVE SUBSTANCE

[75] Inventors: Kjell J. Mattsson; Alf G. M. Nicklasson; Rolf Sjöovist, all of Södertälje, Sweden

[73] Assignee: Astra Lakemedel Aktiebolag, Sodertalje, Sweden

[21] Appl. No.: 584,385

[22] Filed: Sep. 17, 1990

Related U.S. Application Data

[63] Continuation of Ser. No. 127,918, Dec. 2, 1987, abandoned.

[30] Foreign Application Priority Data

Dec. 22, 1986 [SE] Sweden ................. 8605515

[51] Int. Cl.$^5$ ............... A61K 9/16; A61K 9/50; A61K 31/43
[52] U.S. Cl. ................. 424/490; 424/494; 424/498; 424/502; 514/192; 514/937; 514/936; 514/965
[58] Field of Search ............ 424/451, 458, 455, 461, 424/468, 484, 502, 450, 457, 489, 490, 495, 498, 494; 314/962, 963, 965, 78, 937, 192

[56] References Cited

U.S. PATENT DOCUMENTS 3,879,511  4/1975  Goodhart et al. ............. 424/495
4,656,027  4/1987  Sjoovist ....................... 424/495

FOREIGN PATENT DOCUMENTS 101418  2/1984  European Pat. Off. .
0257915 2/1988  European Pat. Off. .
3435747 4/1985  Fed. Rep. of Germany .
78036613 3/1980  Sweden .
1380206 8/1975  United Kingdom .
2166651 5/1986  United Kingdom .
8100205 2/1981  World Int. Prop. O. .
8503000 7/1985  World Int. Prop. O. .

OTHER PUBLICATIONS

Chemical Abst. 87:29032u, 1977.
Chem. Abst. 90:127534r, 1979.
Chem. Abst. 95:181384a, 1981.
Chem. Abst. 99:93779t, 1983.
Chem. Abst. 85:25402a, 1976.
Chem. Abst. 86: 47269k, 1977.

*Primary Examiner*—John W. Rollins
*Attorney, Agent, or Firm*—White & Case

[57] ABSTRACT

A dosage form for oral administration of a pharmaceutically active substance characterized in that it includes a encapsulated or embedded pharmaceutically active substance in a pharmaceutically acceptable non-aqueous liquid.

8 Claims, No Drawings

LIQUID DOSAGE FORM FOR ALL ORAL ADMINISTRATION OF A PHARMACEUTICALLY ACTIVE SUBSTANCE This application is a continuation of application Ser. No. 127,918 filed Jan. 2, 1987, now abandoned.

TECHNICAL FIELD

The present invention relates to a liquid dosage form for oral administration containing microspheres or microcapsules of a pharmaceutically active substance which substance has either an unpleasant taste or which substance is unstable in aqueous solution or both.

The present invention also relates to a method of masking unpleasant taste of a pharmaceutically active substance administered in the form of a solution or suspension and to increase the stability properties of an unstable pharmaceutically active substance administered in the form of a solution or suspension using a non-aqueous liquid carrier.

BACKGROUND OF THE INVENTION

Many pharmaceutically active substances have a very unpleasant taste, and they are therefore not suited for oral administration in the form of solutions or suspensions. Because the administration by solutions or suspensions is a very suitable one and in some cases the only oral way feasible, (e.g. when a patient can not accept tablets or capsules) the problem is a serious one. Thus, for administration to children and elderly, oral suspensions or solutions may be advantageous. In the former case, taste is very important in order to have a high patient compliance.

The problem of masking the unpleasant taste of a pharmaceutically active substance in connection with a liquid dosage form for oral adminis-tration and where the substance is microencapsulated has been tackled in different ways.

In EP 69097 the combination of a microencapsulated active substance with a basic substance prior to preparing a ready to use aqueous suspension is described.

In EP 101418 the combination of a microencapsulated active substance with a high content of sugar prior to preparing a ready to use aqueous suspension is described.

The object of the present invention is to provide a ready to use solution or suspension of a pharmaceutically active substance intended to be administered orally wherein the unpleasant taste of the substance has been masked by combining the principles of microencapsulation and a non-aqueous liquid carrier wherein the encapsulated drug is practically insoluble.

Many pharmaceutically active compounds degrade when dissolved in aqueous or hydrophilic solvents. In order to delay this mechanism, preparations have been formulated where the active compound is reconstituted with water prior to use. In many cases, the suspensions or solutions need to be stored in a cold place. A great improvement would therefore be to have a stable formulation from the manufacturer where the active compound is already suspended in a liquid vehicle. However, when it is not possible to make an ready to use suspension, due to physicochemical reasons, the application of microencapsulation using a coating not requiring a halogenated alkyl solvent or any other related harmful organic solvent or embedding the active compound in a water repellant micro matrix or a sphere can be used in order to increase the solid state stability. Thus, the microspheres or microcapsules can also be mixed with a granulation for reconstitution which creates a more stable system compared to a conventional granu-lation for reconstitution.

A further object of the invention is therefor to increase the stability of a pharmaceutically active substance which is unstable in aqueous or hydrophilic solution or suspension.

A still further object of the invention is to provide controlled release properties of the dosage form according to the invention, thus combining a controlled release with good taste and high stability.

DISCLOSURE OF THE INVENTION

Aqueous suspensions have been used in all prior attempts to tackle the problem of masking unpleasant taste of a liquid oral formulation using a microencapsulated pharmaceutically active substance.

It has now been found that the unpleasant taste of a pharmaceutically active compound intended to be administered orally in the form of a solution or a suspension can be masked if the active compound which must be microencapsulated or embedded in a micromatrix formed from waxes, fats, oils, higher fatty acids and higher alcohols is mixed with a vehicle which consists of a pharmaceutically acceptable non-aqueous liquid, in which the encapsulated drug shows no or extremely low solubility. Hence, it is the combination of a microencapsulated drug and the application of a non-aqueous liquid carrier which makes this particular invention unique.

The present invention provides an improved liquid delivery system for active compounds which have an unpleasant taste. It is also advantageous compared to conventional suspensions or solutions since it prevents the active compound from degrading in the liquid medium. The mechanism behind this phenomenon is first the application of a liquid carrier in which the active compound is not soluble or soluble to a very low extent and secondly the fact that the active compound is microencapsulated or embedded in a micromatrix system. Since the active compound is embedded in a micromatrix structure or is microencapsulated the risk for obtaining an unpleasant taste in the mouth due to dilution or washing of the non-aqueous liquid is reduced due to a delayed release of the active compound from the matrices or microcapsules in aqueous media. The combination of these two factors is a solid ground for obtaining the above mentioned properties. However, as mentioned above, the application of micromatrices or microcapsules may also be advantageous for a granulation for aqueous reconstitution in terms of solid state stability before reconstitution.

By replacing the aqueous vehicle with a non-aqueous vehicle and by microencapsulating or embedding the active compound in a matrix sphere the following advantages are obtained:

The active substance can be prepared in a liquid formulation which is ready to use.

These types of formulations are otherwise normally delivered as a dry powder which has to be mixed with water prior to use. Such a product has relatively bad keeping qualities. Besides, this operation is costly in countries where the pharmacies fullfill them. In countries where the patient himself has to add water the risk of mistakes could not be disregarded. In a manufacturing point of view it is often advantageous to handle a liquid product instead of a dry powder and thus avoiding problems in connection with the production environment.

The formulation of a microencapsulated active substance in a non-aqueous vehicle not only provides masking of an unpleasant taste but affords also enhanced stability. This property is particularly valuable in connection with compounds normally unstable in liquid vehicles, for instance penicillins. No harmful solvents are required in the encapsulation.

Furthermore the formulation according to the invention affords controlled release properties to the formulation.

All those pharmaceutically active substances which have an unpleasant taste or which are unstable in solution are well suited for use in connection with this invention. Examples of such active substances are

| | |
|---|---|
| Chemoterapeutics | bacampicillin, ampicillin, flucloxacillin, tetracycline, dicloxacillin, chloramphenicol, gentamicin, erythromycin, lincomycin, rifampicin, sulphadiazine, sulphamethoxypyridazine, griseofulvine, nitrofurantoine, penicillin V, penicillin G, cephalosporin derivatives. |
| Adrenergic and betareceptor-stimulators | ephedrine, terbutaline, theophylline, enprophylline |
| Expectorants and cough depressants | Ethylmorphine, dextromethorphan, noscapine, bromhexine |
| Heart glucosides and antiarythmics | Digitoxine, digoxin, dispyramide, procainide, tocainide, alprenolol, atenolol, metoprolol pindolol, propranolol |
| Blood pressure depressants | betanidine, clonidine, guanetidine, methyldopa, reserpine, trimetaphane, hydrolazine, bendrophlumetiazide, furosemide, chlorotiazide |
| Antihistamines | brompheniramine, chlorcyclizine, chlorpheniramine, diphenhydramine, prometazine |
| Peroral antidiabetes | carbutamide, chlorpropamide, tolazamide, tolbutamide |
| Sedatives Hypnotics Antidepressants Antipsychotics | meprobamate, chlordiazepoxide, diazepam, buspirone, flunitrazepam, nitrazepam, oxazepam, chloromethiazol, chlorpromazine, fluphenazine, perphenazeine prochloroperazin, haloperidol, lithium, alaproclate, zimeldine, amitryptiline, imipramine, nortriptyline, remoxipride, raclopride |
| Antiepileptics | phenytoine, ethotoin, ethosuximide, carbamazepine |
| Analgetics Anesthetics | codeine, morphine, pentazocine, petidine, dextropropoxyphene, methadone, acetylsalicylic acid, diflunisal, phenazone, phenylbutazon, acetaminophene, indometazine, naproxen, piroxicam, lidocaine, etidocaine |
| Others | cimetidine, quinidine, dicoumarine, warfarine, potassium chloride, chloroquine |

Preferred active substances are remoxipride, raclopride, penicillins, cephalosporins, alaproclate, buspirone, diazepam and other bensodiazepins.

Particularly preferred compounds are remoxipride, acetaminophen, phenoxymethylpenicillin, bacampicillin, bensylpenicillin, flucloxacillin and cephalosporin derivatives.

The active substances mentioned above are used in neutral or salt form.

Any salts of the active substances mentioned above can be used, for instance

Acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malte, maleate, mandelate, mesylate, methylbromide, methylnitrate, methylsulfate, mucate, napsylate, nitrate, pamoate, (embonate), pantothenate, phosphate/diphosphate, polygalacturonate, salicylate, stearate, subacetate, succinate, sulphate, tannate, tartrate, teoclate, triethiodide.

Also the further cationic salts can be used. Suitable cationic salts include the alkali metal, e.g. sodium and potassium, and ammonium salts and salts of amines known in the art to be pharmaceutically acceptable, e.g. glycine, ethylene diamine, choline, diethanolamine, triethanolamine, octadecylamine, diethylamine, triethylamine, 1-amino-2-propanol-2-amino-2-(hydroxymethyl)propane-1,3-diol and 1-(3,4-dihydroxyphenyl)-2-isopropylaminoethanol.

Coating and matrix materials

The techniques for the formation of microencapsulated and matrix material are well known in the art and do not form any part of the present invention.

Coating materials which do not require the use of a halogenated alkyl solvent such as methylene chloride are selected from the group consisting of carnuba wax, ethylcellulose and a combination of carnuba wax and bees wax.

The microcapsules or micromatrices useful for the present invention can be prepared by any of several acknowledge of microencapsulation processes or microsphere or matrix production processes including pan coating, prilling, extrusion and spheronization, fluid bed processes, spray drying, spray chilling coacervation and other processes.

Microspheres, microcapsules or matrix beads in the size range of 10–1000 microns are suitable for being suspended in the liquid carrier. Preferably, the size range of 50–150 $\mu$m are used since this size range is small enough in order to give a smooth appearance in the mouth which is especially important for pediatric formulations. This size range can easily be obtained by means of e.g. spray chilling or spray drying and these processes are also suitable for generating controlled release microcapsules in the same size range. The size range of 50–150 $\mu$m is also preferred because of the low risk of crushing the spheres between the teeth after administration as it might be for larger beads.

The encapsulation of the drug can be achieved in the form of microcapsules, but the encapsulation is not restricted to the micro size.

Microcapsules

Microcapsules are defined as a solid or a liquid core enclosed in a coating. The coating may also be referred to as the wall or shell. Various types of microcapsule structures can be obtained depending on the manufacturing process, e.g. mononuclear spherical, multinuclear spherical, multinuclear irregular, encapsulated mononuclear capsules, dual-walled microcapsules etc. When no distinct coating and core region can be observed, the analogous terms are microparticles, microspheres, micromatrices or microbeads (c.f. multinuclear microcapsules above). The microcapsules usually have a particle size between 1 and 2000 $\mu$m. The preferred size range for this invention is 50-150 $\mu$m.

The microcapsules referred to in the present invention can thus be designed as micromatrices, overcoated micromatices or overcoated homogeneous microsphere cores.

Non-aqueous vehicle

Non-aqueous vehicle is a pharmaceutically acceptable non-aqueous liquid such as a pharmaceutically acceptable oil, e.g. hydrogenated coconut oil, such as Miglyol ® and Viscoleo ®, coconut oil, peanut oil, sesam oil, corn oil.

Emulsifying agents

Emulsifying agents (super active agents) to be used are for instance:
 bile salts or derivatives thereof
 propyl gallat
 sorbiton fatty acid esters
 polyoxyethylene sorbiton fatty acid esters
 polyoxyethylene sorbitol esters
 polyoxyethylene acids
 polyoxyethylenel alcohols
 polyoxyethylene adduch not otherwise classified
 mono and diglycerides
 polyoxyethylene glyceryl fatty acid esters
 fusidic acid derivatives
 sodium lauryl sulphate Preferred embodiments A preferred embodiment of the present invention is obtained when remoxipride is encapsulated in carnauba wax and mixed with a vehicle consisting of hydrogenated coconut oil.

Other preferred embodiments are obtained when phenoxymethyl penicillin, bacampicillin, bensylpenicillin, flucloxacillin or acetaminophene are encapsulated in carnauba wax and mixed with a vehicle consisting of hydrogenated coconut oil.

Still other preferred embodiments are obtained when the active substance is encapsulated in either carnauba wax and beeswax or in ethyl cellulose, carnauba wax and bees wax and mixed with a vehicle consisting of hydrogenated coconut oil.

Still another preferred embodiment is obtained when the active substance is encapsulated in either cannauba wax, bees wax, cannauba wax and bees wax or ethyl cellulose and mixed with a vehicle consisting of hydrogenated coconut oil and a suitable emulsifying agent, e.g. bile salts.

The preparation is preferably made by adding the solid powders (i.e, flavouring agents and sugars) to the fluid component by mixing until a homogeneous suspension is obtained. Finally the microcapsules are added and gently mixed. The suspension can then be added to glass or plastic bottles. In some cases, a thickening agent is preferable to prevent a too rapid sedimentation of the suspended particles (e.g. aluminum monostearate, stearic acid, bees wax etc.)

Best mode of carring out the invention

EXAMPLE 1

Remoxipride substance with a particle size less than 10 μm was suspended in a carnauba wax melt at 100° C. The slurry was spray chilled into microspheres with a diameter between 50 and 125 μm.

| Remoxipride microspheres consist of: | |
|---|---|
| Remoxipride hydrochloride monohydrate | 40% |
| Carnauba wax | 60% |
| Composition of an oral suspension: | |
| Remoxipride microcapsules | 13.5 g |
| Sodium bicarbonate | 0.84 g |
| Caramel flavour | 0.50 g |
| Sucrose powder | 35.50 g |
| Hydrogenated coconut oil | 60.00 g |

In a beaker the oil was added and the sucrose powder was added in small portions while stirring vigorously. Sodium bicarbonate and the flavouring component were added and finally the remoxipride microcapsules were added. The resulting product was a free flowing suspension with a nice appearance.

The taste of this product was judged by 10 people and was compared to an aqueous solution with the same concentration of remoxipride. The people was asked to judge if the product was acceptable from a taste point of view compared to the plain remoxipride solution.

| | Results: | |
|---|---|---|
| | Acceptable | Not acceptable |
| The composition according to ex 1 | 10 | 0 |
| Remoxipride aqueous solution | 0 | 10 |

The invented product was superior to a non taste masked aqueous product. Thus the invented product has a very high degree of taste masking as the plain solution has a very bitter taste, which was the main comment from the test panel for the plain remoxipride solution.

EXAMPLE 2

A suspension according to the present invention, containing remoxipride microspheres (40% remoxipride and 60% wall material) was filled in no. 1 hard gelatin capsules. The capsules were administered to two male beagle dogs, and plasma was collected. As reference a solution of remoxipride was used. The dose of the oil suspension (the invented product) was 215 μmol and the solution was 250 μmol of remoxipride. The plasma concentrations of remoxipride were analyzed with a high pressure liquid chromatography method.

The maximum plasma concentration obtained ($C_{max}$) and the extent of bioavailability (AUC) are shown in the Table.

The $C_{max}$ reflects the highest concentration of the drug. A drug that absorbs rapidly reaches a high $C_{max}$-value than if it absorbs slowly. The area under the plasma concentration vs. time curve (AUC) reflects the amount of the drug that has been absorbed during the experimental period.

| | Results: | | | |
|---|---|---|---|---|
| | $C_{max}$ μmol/l | | AUC μmol × h/l | |
| | Dog 1 | Dog 2 | Dog 1 | Dog 2 |
| The invented product | 10.5 | 9.4 | 72 | 56 |
| Remoxipride solution | 11.9 | 11.2 | 72 | 58 |

It can easily be seen that the invented product is bioequivalent to a plain solution of remoxipride. As a matter of fact, if corrections are made for the dosing difference the invented product has 9 and 4 percent better bioavailability in the two dogs respectively. Thus, the taste masking efforts have no negative effect upon the biopharmaceutical properties of the drug.

EXAMPLE 3

Controlled release microcapsules were prepared by means of spray chilling. The particles consisted of 16% remoxipride hydrochloride monohydrate and 84% carnauba wax/bees wax. Particles with a size between 53 and 106 μm were collected and used for further experiments.

The release rate of remoxipride from the microcapsules in water at 37° C. is given below:

| Percent (%) remoxipride released | | | | |
|---|---|---|---|---|
| 1 h | 2 h | 4 h | 6 h | 8 h |
| 56 | 66 | 80 | 86 | 92 |

The controlled release microcapsules were added to an oil formulation.

| Composition: | |
|---|---|
| Remoxipride controlled release microcapsules described above: | 8.3 g |
| Caramel flavour | 0.5 g |
| Peppermint oil | 0.5 g |
| Sucrose powder | 41.0 g |
| Hydrogenated coconut oil | 60.0 g |

Caramel flavour, peppermint oil and sucrose powder were added to the oil and mixed vigorously. Then the controlled release microcapsules were added and gently mixed. The resulting product has thus controlled release properties and it is also taste masked.

EXAMPLE 4

Dual-walled controlled release microcapsules were prepared by means of spray drying and spray chilling. The microcapsule core consisted of remoxipride hydrochloride monohydrate and ethyl cellulose. The cores were then overcoated with carnauba wax and bees wax, respectively. Particles with a size between 50 and 150 μm were collected and used for further experiments. The final content of remoxipride hydrochloride monohydrate was found to be 16%.

The release rate of remoxipride from the microcapsules in water at 37° C. is given below:

| Percent (%) remoxipride released | | | | | | | |
|---|---|---|---|---|---|---|---|
| 2 h | 4 h | 6 h | 8 h | 10 h | 15 h | 20 h | 24 h |
| 30 | 38 | 45 | 53 | 58 | 70 | 76 | 81 |

The controlled release microcapsules were added to an oil formulation.

| Composition: | |
|---|---|
| Dual-walled remoxipride controlled release microcapsules | 15.6 g |
| Caramel flavour | 0.5 g |
| Peppermint oil | 0.5 g |
| Sucrose powder | 35.4 g |
| Hydrogenated coconut oil | 60.0 g |

Caramel flavour, peppermint oil and sucrose powder was added to the oil and mixed vigorously. Then the controlled release microcapsules were added and gently mixed. The resulting product has controlled release properties and it is also taste masked.

EXAMPLE 5

Phenoxymethyl penicillin —K microcapsules consist of

| Phenoxymethyl penicillin -K | 40% |
|---|---|
| Carnauba wax | 60% |

The penicillin powder with a particle size less than 10 μm was suspended in a carnauba wax melt at 105° C. The slurry was spray chilled into microspheres with a diameter between 50 and 125 μm.

Composition of an oral suspension:

| Phenoxymethyl penicillin -K microcapsules | 11.6 g |
|---|---|
| Lemon flavour | 0.42 g |
| Strawberry flavour | 0.70 g |
| Maltol | 0.28 g |
| Sucrose powder | 30.4 g |
| Hydrogenated coconut oil | 56.5 g |

The taste of this product was judged by seven people and was compared to a phenoxymethyl penicillin —K suspension on the market with the same dosage strength (KÅVEPENIN 50 mg/ml). The table summarizes the taste scores obtained where 0 denotes a very bad taste and 100 denotes a perfect taste.

| Subject no. | New suspension | Market suspension |
|---|---|---|
| 1 | 91 | 80 |
| 2 | 92 | 54 |
| 3 | 93 | 79 |
| 4 | 78 | 31 |
| 5 | 91 | 74 |
| 6 | 91 | 47 |
| 7 | 77 | 82 |
| x | 87.6 | 63.9 |

The data demonstrate a much better acceptance for the new type of suspension of phenoxymethyl penicillin —K. Also, the taste profile is more irregular for the market suspension and more uniform for the new one which shows that the new suspension has a much better taste in general.

EXAMPLE 6

Bacampicillin hydrochloride substance with a particle size less than 10 μm was suspended in a carnauba wax melt at 100° C. The slurry was spray chilled into microcapsules with a diameter between 50 and 125 μm.

Bacampicillin hydrochloride microcapsules consist of

| Bacampicillin hydrochloride | 25% |
|---|---|
| Carnauba wax | 75% |
| Composition of an oral suspension | |
| Bacampicillin microcapsules | 14.14 g |
| Strawberry flavour | 1.30 g |
| Lemon flavour | 0.69 g |
| Maltol | 0.29 g |
| Sucrose powder | 25.08 g |
| Hydrogenated coconut oil | 58.51 g |

EXAMPLE 7

Bacampicillin hydrochloride substance with a particle size less than 10 μm was suspended in a carnauba wax melt at 100° C. The slurry was spray chilled into microcapsules with a diameter between 50 and 125 μm.

Bacampicillin hydrochloride microcapsules consist of

| Bacampicillin hydrochloride | 40% |
|---|---|
| Carnauba wax | 60% |
| Composition of an oral suspension | |
| Bacampicillin microcapsules | 8.81 g |
| Strawberry flavour | 1.30 g |
| Lemon flavour | 0.69 g |
| Sucrose powder | 20.00 g |
| Hydrogenated coconut oil | 58.51 g |

EXAMPLE 8

Phenoxymethyl penicillin —K substance with a particle size less than 10 μm was suspended in a carnauba wax melt at 100° C. The slurry was spray chilled into microcapsules with a diameter between 50 and 125 μm.

Phenoxymethyl penicillin —K microcapsules consist of

| Phenoxymethyl penicillin -K | 40% |
|---|---|
| Carnauba wax | 60% |
| Composition of an oral suspension | |
| Phenoxymethyl penicillin microcapsules | 15.63 g |
| Strawberry flavour | 0.35 g |
| Lemon flavour | 0.15 g |
| Sucrose powder | 61.91 g |
| Hydrogenated coconut oil | 70.00 g |

The stability of this product was investigated during storage at 25° C. and 37° C. for four months. The table shows the assayed quantity of degradation product (mg penicilloic acid/g suspension).

| Storage Time | 25° C. | 37° C. |
|---|---|---|
| 0 | 0.20 mg/g | 0.20 mg/g |
| 4 months | 0.45 mg/g | 0.60 mg/g |

The result in the table shows that the invented formulation of phenoxymethylpenicillin —K is very stable. An increase of only 0.4 mg/g of penicilloic acid is obtained after 4 months' storage at an accelerated storage condition (37° C.) This corresponds only to about 1% in relation to the phenoxymethylpenicillin —K concentration in the suspension.

EXAMPLE 9

Bensylpenicillin —K substance with a particle size less than 10 μm was suspended in a carnauba wax melt at 100° C. The slurry was spray chilled into a microcapsules with a diameter between 50 and 125 μm.

Bensylpenicillin =K microcapsules consist of

| Bensylpenicillin -K | 40% |
|---|---|
| Carnauba wax | 60% |
| Composition of an oral suspension | |
| Bensylpenicillin -K microcapsules | 11.6 g |
| Lemon flavour | 2.2 g |
| Strawberry flavour | 2.8 g |
| Sucrose powder | 41.1 g |
| Hydrogenated coconut oil | 54.7 g |

EXAMPLE 10

Flucloxacillin —Na substance with a particle size less than 10 μm was suspended in a carnauba wax melt at 100° C. The slurry was spray chilled into microcapsules with a diameter between 50 and 125 μm.

Flucloxacillin —Na microcapsules consist of

| Flucloxacillin -Na | 36% |
|---|---|
| Carnauba wax | 64% |
| Composition of an oral suspension | |
| Flucloxacillin -Na microcapsules | 6.41 g |
| Strawberry flavour | 1.32 g |
| Lemon flavour | 0.70 g |
| Maltol | 0.26 g |
| Sucrose powder | 31.95 g |
| Hydrogenated coconut oil | 59.34 g |

EXAMPLE 11

1.0 g of polyisobutylene was dissolved in 200 ml of cyclohexane under stirring and heating up to 80° C. After the polyisobutylene was dissolved 1.0 g of ethylcellulose was dissolved. To the cyclohexane solution 2.0 g of Remoxipride hydrochloride monohydrate powder was suspended. Under stirring and controlled cooling, the resulting coated particles were collected and filtered off. The coated particles, or microcapsules, were washed with cool cyclohexane and then air-dried.

| Composition: | |
|---|---|
| Microcapsules described above | 2.0 g |
| Butterschotch flavour | 0.1 g |
| Sodiumbicarbonate | 0.1 g |
| Sucrose powder | 3.0 g |
| Peanut oil | 8.0 g |

The microcapsules, flavour, sodium bicarbonate and sucrose were added to the peanut oil and gently mixed. The resulting oral suspension was not tasting any bitterness of remoxipride.

What is claimed is:

1. An oral pharmaceutical dosage form comprising an encapsulated pharmaceutically active substance and a pharmaceutically acceptable nonaqueous liquid wherein the active substance is encapsulated in a coating, selected from the group consisting of ethylcellulose, carnauba wax and a combination of carnauba wax and beeswax which coating is applied by spray drying and spray chilling in an a solvent system which does not contain a halogenated solvent.

2. An oral pharmaceutical dosage form comprising an encapsulated pharmaceutically active substance and a pharmaceutically acceptable nonaqueous liquid wherein the active substance is encapsulated in a first coating of ethylcellulose which is then coated with a second coating comprising a combination of carnauba wax and beeswax, the encapsulation being effected by spray drying and spray chilling, in a solvent system which does not contain a halogenated solvent.

3. A dosage form according to either of claims 1 or 2, wherein the active substance is remoxipride.

4. A dosage form according to either of claims 1 or 2, wherein the active substance is selected from the group consisting of bacampicillin, penicillin V, benzylpenicillin and flucloxacillin.

5. An oral pharmaceutical dosage form according to either of claims 1 or 2, wherein the nonaqueous liquid is a pharmaceutically acceptable oil.

6. An oral pharmaceutical dosage form according to claim 15 wherein the pharmaceutically acceptable oil is hydrogenated coconut oil.

7. A process for the preparation of an oral pharmaceutical dosage form comprising adding solid adjuvants to a nonaqueous liquid, mixing the adjuvants and the nonaqueous liquid until a homogeneous suspension is obtained, and adding a pharmaceutically active substance encapsulated in a coating, selected from the group consisting of ethylcellulose, carnauba wax and a combination of carnauba wax and beeswax which is applied by spray drying and spray chilling in a solvent system which does not contain a halogenated solvent in the encapsulation procedure.

8. A process according to claim 7 wherein the active substance is encapsulated in a first coating of ethylcellulose and a second coating comprising a combination of carnauba wax and bees wax.

* * * * *